United States Patent [19]
Andreasen

[11] Patent Number: 4,900,251
[45] Date of Patent: Feb. 13, 1990

[54] ORTHODONTIC ARCHWIRE, APPARATUS, PACKAGE AND METHOD

[75] Inventor: George F. Andreasen, deceased, late of Iowa City, Iowa, by Merritt Andreasen and First National Bank, Executors

[73] Assignee: University of Iowa Research Foundation, Iowa City, Iowa

[21] Appl. No.: 187,735

[22] Filed: Apr. 29, 1988

[51] Int. Cl.⁴ .............................................. A61C 7/00
[52] U.S. Cl. ..................................................... 433/20
[58] Field of Search ................................... 433/20, 22

[56] References Cited

U.S. PATENT DOCUMENTS

| | | | |
|---|---|---|---|
| 1,103,606 | 7/1914 | Montag | 433/20 |
| 3,055,110 | 9/1962 | Kesling | 433/17 |
| 3,916,526 | 11/1975 | Schudy | 433/20 |
| 4,268,250 | 5/1981 | Reeve | 433/20 |
| 4,424,033 | 1/1984 | Reeve | 433/20 |

OTHER PUBLICATIONS

Cover, p. 10 and p. 11 from brochure entitled "A Guide for Using Nitinol Activ-Arch Wire".

Primary Examiner—Robert Peshock
Attorney, Agent, or Firm—Beveridge, DeGrandi & Weilacher

[57] ABSTRACT

Mesial-distal slippage of an orthodontic archwire is deterred by manufacturing a parabolic archwire with a bend at its vertex. The bend has a height incapable of entering the wire-receiving slots of the brackets on a patient's teeth.

23 Claims, 1 Drawing Sheet

FIG. 1
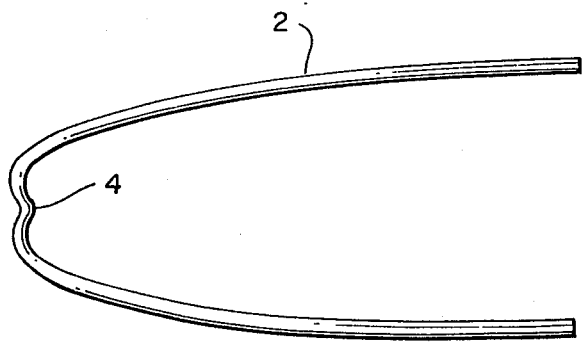
FIG. 2
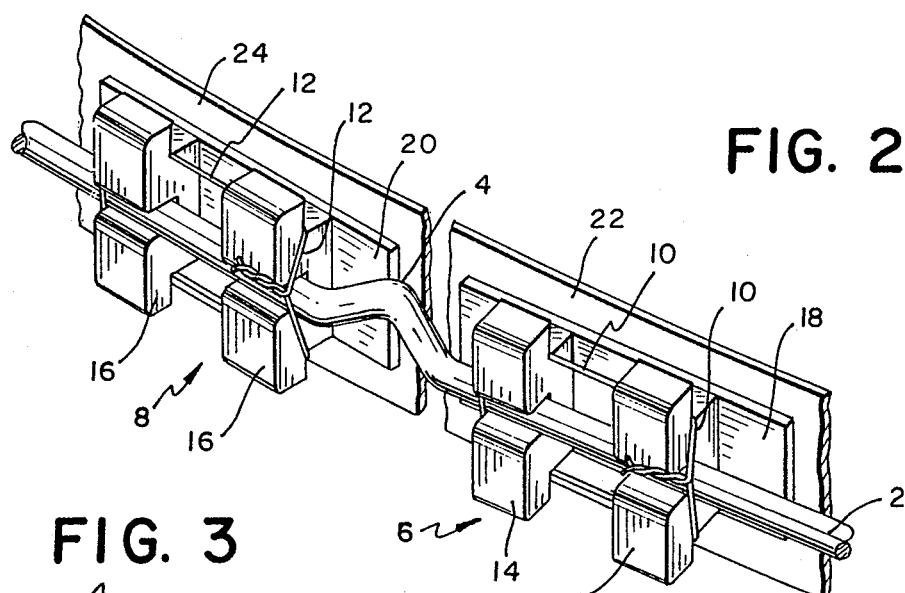
FIG. 3
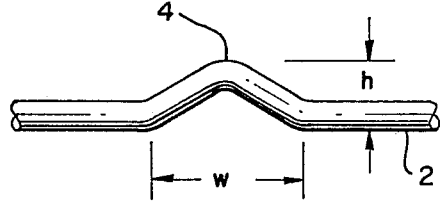
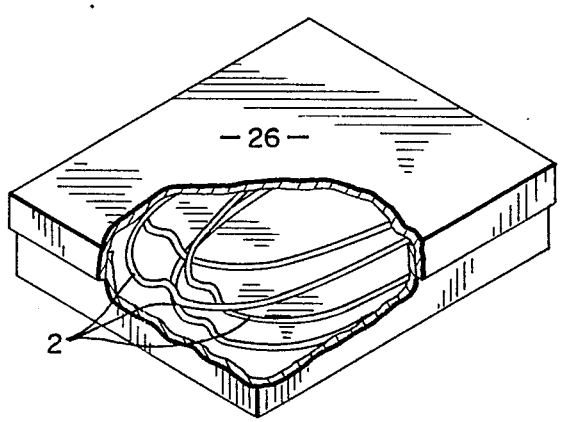
FIG. 4
FIG. 5

ORTHODONTIC ARCHWIRE, APPARATUS, PACKAGE AND METHOD

BACKGROUND

This invention relates to improvements in the field of orthodontics. It presents a new solution to a problem which has arisen with some modern archwires because they cannot easily be bent at their ends to prevent them from slipping excessively lengthwise, i.e. in the mesial-distal direction.

According to conventional orthodontic practice, a plurality of wire-receiving brackets are banded or bonded to the teeth, except that the distal molars are provided with tubes. A parabolic archwire has its opposite ends inserted in the molar tubes, and the archwire is inserted into wire-receiving slots of the brackets on the teeth. Ligature wires are used to tie the wire to the brackets. When attached to the brackets, the wire is under flexural and/or torsional stresses which, due to the resiliency of the wire, exert corrective tooth-moving forces on the teeth.

Until the advent of ultraelastic wires such as those formed of shape memory alloys as disclosed in my earlier U.S. Pat. No. 4,037,324, it was customary orthodontic practice to form bends in the distal ends of stainless steel archwires immediately at the distal ends of the molar tubes. However, when using wires formed of shape memory alloys, such as those disclosed in U.S. Pats. 4,037,324 and 4,490,112, the physical properties of the wires resist the formation of an effective distal bend. Without a distal bend, a wire is free to slide lengthwise, i.e. in a mesial-distal direction, until one end protrudes excessively from a molar tube so it contacts, irritates, and produces ulcerations in the patient's mouth. This problem can be accentuated when the coefficient of friction between the wire and the brackets is relatively low, and when there are no bends or auxiliaries formed in or attached to the archwire. Although V-shaped bends have been formed in archwires for the attachment of hooks and other devices, no manufacturer or supplier has provided archwires which are prevent to reduce the extent of sliding movement of the wires relative to the brackets and molar tubes.

Conventional brackets to which the invention is applicable have slots with measurements of 0.018 to 0.022 inch in the gingival-occlusal direction, when used with wires of square, round or rectangular cross section measuring, 0.014 to 0.0215 inch in the gingival-occlusal direction. Presently available small edgewise brackets have wire-receiving slots which measure 018 inch and, 0.025 inch, respectively, in the gingival-occlusal and buccal-lingual directions. The corresponding measurements of the slots in heavy edgewise brackets measure 0.022 and 0.028 inch. Small and large edgewise brackets are used with round wires with diameters of 0.014, 0.016 and 0.018 inch; square wires measuring 0.016, 0.017 and 0.018 inch; and, rectangular wires measuring 0.016 ×0.022 inch, 0.016 ×0.025 inch, 0.017 ×0.022 inch, 0.017 ×0.025 inch, 0.018 ×0.022 inch, and 0.018 ×0.025 inch. Additionally, large edgewise brackets are used with 0.020 inch and 0.022 inch round wires, 0.020 inch square wires, and rectangular wires which are 0.019 ×0.026 inch, 0.021 ×0.022 inch, 0.021 ×0.025 inch, and 0.0215 ×0.028 inch.

SUMMARY OF THE INVENTION

According to one aspect of the invention, an orthodontic archwire is a single piece of wire having a generally parabolic shape, with a slip-preventing lateral protrusion being provided approximately midway along the length of the wire. The lateral protrusion has a direction and size which is incapable of slipping through slots in orthodontic brackets. Preferably, the lateral protrusion is a bend formed in the wire to occupy about 1 to 3 mm of the length of the wire. The bend has an overall height of at least 0.7 mm, and it has two legs which are equal in height and opposite in direction.

The invention also involves an orthodontic apparatus including the type of archwire described in the preceding paragraph associated with orthodontic brackets which are attached to the central incisors of an orthodontic patient. Due to the inability of the lateral protrusion to slide through the bracket slots, the sliding movement of the archwire is limited in a mesial-distal direction.

Another feature of the invention is a package which is used for supplying archwires to orthodontists. This package includes a container, and a plurality of archwires which are in the container. Each archwire has a localized lateral protrusion with a size and shape which is incapable of sliding through a bracket slot so that, when the wire is connected to orthodontic brackets in a patient's mouth, the presence of the protrusion will limit the extent of sliding movement of the wire. Preferably, the archwires are of the type described above.

A further feature of the invention pertains to the manufacturing and handling of orthodontic archwires whereby they are formed and shaped so that each wire is parabolic and has a lateral protrusion which has a size incapable of passing through the slot of an orthodontic bracket. A plurality of such archwires are sent from the manufacturing facility to an orthodontist for installation in patient's mouths.

BRIEF DESCRIPTION OF THE DRAWINGS

FIG. 1 is a perspective view of an archwire which is constructed according to the invention.

FIG. 2 is a perspective view of the archwire of FIG. 1 which is attached to brackets on the central incisors of an orthodontic patient.

FIG. 3 is an enlarged frontal view of the bent portion of the wire.

FIG. 4 shows a package which contains a plurality of preformed archwires made according to the invention.

FIG. 5 is a flowchart illustrating some of the method aspects of the invention.

DETAILED DESCRIPTION

An archwire 2 used in connection with this invention is illustrated in FIG. 1. It has a generally parabolic shape and it is formed of an ultraelastic or shape memory alloy such as nitinol, a well-known alloy of nickel and titanium which is presently being used for orthodontic archwires. The vertex of the parabola will be located at the center of the dental arch of a patient where it will lie between orthodontic brackets which are mounted on the central incisors. To this extent, the wire is identical to wires which have been commercially available for years. At the vertex of the archwire, i.e. approximately midway along the length of the parabola, there is a small V-shaped bend 4 formed in the wire. This bend constitutes a lateral protrusion which will prevent excessive slipping or sliding movement of the wire in a mesial-distal direction when installed in an orthodontic system. The bend can be formed with contouring pliers of the type commonly used in the practice of orthodontics, but it preferably is performed between a pair of matched dies for uniformity and to avoid or reduce any curvature adjacent to the bend in the gingival-occlusal direction. The use of dies for this purpose is not a feature of the present invention.

The principle of the invention will be understood by referring to FIG. 2 which shows the vire tied to brackets 6 and 8 which are mounted on the central incisors of a patient's mouth. These brackets are conventional siamese brackets which have wire-receiving slots and ears. Ligature wires 10 and 12 are attached to the ears 14 and 16 in order to hold the archwire in the bracket slots. The brackets have bases provided with means for attaching them to teeth with adhesive or with a circumferential band 22 and 24 as is well known in orthodontic practice. As will be evident from FIG. 2, the protrusion resulting from the V-shaped bend is sufficiently large than it cannot slip into or through the bracket slots. In this respect, the bend is surrounded so that the wire cannot slip a significant distance along its length which inherently substantially coincides with the mesial-distal axis of the dental arch.

As can be seen in FIG. 3, the overall height h of the wire 2 at the bend 4 is about two times the wire thickness t, and the length 1 of the bent section is about four times the thickness t of the wire. A suitable bend for a 0.018 inch wire has an overall height h of about 0.8 mm. and a length 1 of about 2 mm. The height should be at least about 0.7 mm. so that the bent section cannot slip into and through a bracket slot, and the length of the bend should from about 1 to 3 mm. It will be understood by persons in the art that, in this context, the height is measured in the gingival-occlusal direction, and the length is measured in the mesial-distal direction.

Referring to FIG. 4, it will be seen that a plurality of the archwires 2 are placed in a single box so there is a package including a plurality of archwires with the antislip bends formed therein. This is quite different from conventional practice in which such bends are not made by the manufacturers, and are not present in archwires sent to or received by orthodontic practitioners.

Referring to FIG. 5, it will be seen that the archwire is preshaped at the manufacturing facility into the configuration shown in FIG. 1. This involves the steps of bending it into the parabolic shape and forming the V-shaped bend to provide the lateral protrusion which has a size incapable of passing through the slots of an orthodontic bracket. A plurality of these preformed archwires are then sent from the manufacturer to the orthodontist who then installs them in the mouths of his or her patients, at which time the preformed bends are placed between the central incisor brackets as shown in FIG. 3 to deter the mesial-distal slippage of the wire in the patient's mouth.

Persons familiar with the field of this invention will realize that it may take many forms. The wires may be formed of conventional stainless steel, but they preferably are formed of ultraelastic or shape memory alloys which pose particular problems due to their low coefficients of friction and their resistance to localized bending at the rear of the molar tubes. Suitable alloys are nickel titanium and ternary alloys of copper, zinc and aluminum. Various applicable compositions are disclosed in the Kirk-Othmer Encyclopedia of Chemical Technology, Third Edition volume 20, pages 726-736, John Wiley & Sons, 1982. This publication is incorporated herein by reference. The bend preferably has two legs which are equal in size and opposite in direction, but other shapes are possible. Attachments rather than bends may be used under some circumstances to provide lateral antislip protrusions.

It is emphasized that the invention is not limited only to the disclosed embodiments but is embracing of other wires, systems and methods which fall within the spirit of the following claims.

What is claimed

1. An orthodontic archwire, comprising, a single piece of wire, said wire having a generally parabolic shape and having a slip-preventing lateral protrusion thereon, said lateral protrusion being located approximately midway along the length of the wire so as to lie between brackets mounted on the central incisors of an orthodontic patient, said lateral protrusion having a direction and size which is incapable of slipping through slots in orthodontic brackets.

2. An orthodontic archwire according to claim 1 wherein the lateral protrusion is a bend formed in the wire.

3. An orthodontic archwire according to claim 1 combined with two brackets mounted on the central incisors of an orthodontic patient, said brackets having wire-receiving slots, said archwire lying in said slots, said lateral protrusion lying between said two brackets to limit slipping of said archwire in a mesial-distal direction due to the inability of the protrusion to slip through the bracket slots.

4. An orthodontic archwire according to claim 3 wherein the lateral protrusion is a bend formed in the wire.

5. An orthodontic archwire according to claim 4 wherein the bend occupies a length of about 1 to 3 mm.

6. An orthodontic archwire according to claim 4 wherein said bend has two legs which are equal in height and opposite in direction.

7. An orthodontic archwire according to claim 4 wherein the bend has a height of at least about 0.7 mm.

8. A plurality of orthodontic archwires according to claim 1, a container, said archwires being in said container to provide a package for supplying the archwires to an orthodontist.

9. The invention according to claim 8 wherein the lateral protrusion is a bend formed in the wire.

10. The invention according to claim 9 wherein the bend occupies a length of about 1 to 3 mm.

11. The invention according to claim 9 wherein said bend has two legs which are equal in height and opposite in direction.

12. The invention according to claim 9 wherein the bend has a height of at least about 0.7 mm.

13. An orthodontic apparatus including a plurality of bracket means and an archwire, said apparatus having means for attaching two of said bracket means to the central incisors of an orthodontic patient, each said bracket means having a wire-receiving slot formed therein, said archwire extending through said slots, said archwire having a lateral protrusion thereon at a location which lies between said two brackets, said lateral protrusion having a direction and size which is incapable of sliding through said slots so as to limit sliding movement of the archwire relative to the brackets in a mesial-distal direction.

14. An orthodontic apparatus according to claim 13 wherein the lateral protrusion is a bend formed in the wire.

15. An orthodontic apparatus according to claim 14 wherein the bend occupies a length of about 1 to 3 mm.

16. An orthodontic apparatus according to claim 14 wherein said bend has two legs which are equal in height and opposite in direction.

17. An orthodontic apparatus according to claim 14 wherein the bend has a height of at least about 0.7 mm.

18. A package for supplying archwires to orthodontists, said package including
a container,
a plurality of archwires in said container,
each of said archwires being in the shape of a parabola provided with a localized lateral protrusion which has a size and shape which is incapable of sliding through a slot of an orthodontic bracket so as to limit the extent to which an archwire may slide in a mesial-distal direction when it is connected to orthodontic brackets attached to a patient's teeth,
said lateral protrusion being a V-shaped bend in the wire having a length of about 1 to 3 mm and a height of at least about 0.7 mm.

19. A method of manufacturing and handling orthodontic archwires including the steps of,
preshaping a plurality of archwires at a manufacturing facility, said preshaping step including the steps of forming a wire into a parabolic shape which has a a lateral protrusion at its vertex, said lateral protrusion having a size which is incapable of passing through the notch of an orthodontic bracket, and sending a plurality of preshaped archwires from said manufacturing facility to an orthodontist for installation in the mouths of orthodontic patients.

20. A method according to claim 19 wherein the preshaping step forms a bend which is said lateral protrusion.

21. A method according to claim 20 wherein the preshaping step forms a bend which occupies about 1 to 3 mm. along the length of the wire.

22. A method according to claim 20 wherein the preshaping step forms a bend which has two legs which are equal in length and opposite in direction.

23. A method according to claim 20 wherein the preshaping step forms a bend which has a height of at least about 0.7 mm.

* * * * *